United States Patent
Lin

(10) Patent No.: US 9,782,301 B2
(45) Date of Patent: Oct. 10, 2017

(54) HYDROGEL STRUCTURE

(75) Inventor: Tsu-Tai Lin, Taipei (TW)

(73) Assignee: COMPOSE ELEMENT LIMITED, Taipei (TW)

(*) Notice: Subject to any disclaimer, the term of this patent is extended or adjusted under 35 U.S.C. 154(b) by 0 days.

(21) Appl. No.: 13/462,468

(22) Filed: May 2, 2012

(65) Prior Publication Data

US 2013/0053747 A1 Feb. 28, 2013

Related U.S. Application Data

(60) Provisional application No. 61/527,697, filed on Aug. 26, 2011.

(51) Int. Cl.
| | |
|---|---|
| *A61F 13/00* | (2006.01) |
| *A61F 13/02* | (2006.01) |
| *A61L 15/26* | (2006.01) |
| *A61L 15/42* | (2006.01) |
| *A61L 15/46* | (2006.01) |
| *A61L 15/58* | (2006.01) |
| *A61L 15/60* | (2006.01) |

(52) U.S. Cl.
CPC ........ *A61F 13/022* (2013.01); *A61F 13/0209* (2013.01); *A61F 13/0213* (2013.01); *A61L 15/26* (2013.01); *A61L 15/42* (2013.01); *A61L 15/46* (2013.01); *A61L 15/58* (2013.01); *A61L 15/60* (2013.01); *A61F 2013/00119* (2013.01)

(58) Field of Classification Search
CPC ............ A61F 13/00; A61F 2013/00089; A61F 13/022; A61K 8/00; A61K 8/02; A61K 8/04; A61K 8/042; A61K 2800/00; A61K 2800/40; A61K 2800/48; A61K 2800/54
USPC ...... 602/41, 45, 42, 900, 48, 49, 50, 51, 52; 524/376, 377, 379, 318, 386, 556; 600/306
See application file for complete search history.

(56) References Cited

U.S. PATENT DOCUMENTS

| | | | | |
|---|---|---|---|---|
| 7,999,023 | B2* | 8/2011 | Menon et al. | 524/376 |
| 2001/0049413 | A1* | 12/2001 | Haraguchi | 524/446 |
| 2003/0040691 | A1* | 2/2003 | Griesbach et al. | 602/45 |
| 2009/0297587 | A1 | 12/2009 | Yang et al. | |

(Continued)

FOREIGN PATENT DOCUMENTS

| | | |
|---|---|---|
| CN | 1562382 A | 1/2005 |
| CN | 2008101224381 | 10/2008 |

OTHER PUBLICATIONS

CN Patent app No. 2008101224381 is also published as US2009297587A1.

*Primary Examiner* — Ophelia A Hawthorne
(74) *Attorney, Agent, or Firm* — Hannah M. Tien

(57) ABSTRACT

A hydrogel structure which has: (a) a one way penetrating polyurethane film layer; (b) a hydrophobic pressure sensitive adhesive layer; (c) a multi-directional elastic meltblown nonwoven; (d) an interpenetrating polymer network; and (e) a hydrogel; wherein the meltblown nonwoven and the hydrogel are laminated by UV curing to form the interpenetrating polymer network, part of fibers of the meltblown nonwoven are exposed and fit stably with the pressure sensitive adhesive film. The hydrogel structure can make dressings multi-directional elastic for multiple traumas. The hydrogel structure can provide an environment suitable for wound healing, shorten the healing time, antiseptic and reduce the chances of being infected for the wound dressing.

14 Claims, 9 Drawing Sheets

(56) References Cited

U.S. PATENT DOCUMENTS

| | | | |
|---|---|---|---|
| 2010/0160480 A1* | 6/2010 | Tomko | C08G 18/12 522/174 |
| 2010/0198177 A1* | 8/2010 | Yahiaoui | A61F 13/82 604/359 |
| 2011/0313383 A1* | 12/2011 | Hofstetter et al. | 604/372 |
| 2012/0035294 A1* | 2/2012 | Kim et al. | 522/154 |

* cited by examiner

A

B

A

B

A

B

HYDROGEL STRUCTURE

FIELD OF THE INVENTION

The present invention relates to the field of medical dressing technology, specifically provides a hydrogel structure that can keep a suitable environment for wound healing, shorten the healing time, antiseptic and reduce the chances of being infected.

BACKGROUND OF THE INVENTION

According to recent scientific and statistical reports, the global trauma market is growing demand, especially in surgical trauma; the total people have exceeded 100 million per year and showed an upward trend year by year. People with trauma and lacerations caused by accidents are around 20 million per year. The number of burns is about 10 million people each year. People with ulcerative wounds caused by chronic diseases, diabetes and aging have been more than 30 million per year.

Because of the treatment needs and the popularity of endoscopic surgery, the risks caused by surgery have greatly reduced, but followed by the needs of better postoperative wound care and scar prevention. Currently there have been methods with the help of various advanced wound caring dressings, in order to shorten the healing time and eliminate scars.

The traditional dressings are made of natural plant fibers or animal hair materials such as gauze, cotton pad, wool, and all kinds of oiled gauzes. These dressings are only temporary covering materials that need to be replaced in a certain period of time. The study of wound dressings lets us grow scientific understanding of them. Studies have shown that: a better trauma dressing is to maintain a good environment for cell growth and healing at wound, to control and absorb exudates; breathable, moisture permeable and can prevent bacterial invasion; can closely stick to the surface of wounds; can carry and release the drug; also should have good tissue and blood compatibility that when taking it off from the wound surface, no adhesion and desquamation occurs; and also should have better mechanical properties and tensile strength, easy to use. In existing technology, such as published on Oct. 29, 2008 China patent application No. 200810122438.1 provided a preparation method for medical hydrogel bed dressing, and the patent published on Jan. 12, 2005 issue No. CN1562382A named "Water emulsion containing polyurethane-based hydrogel wound dressing and preparation method" is about a hydrogel as a base for medical dressing.

SUMMARY OF THE INVENTION

Figure 1:
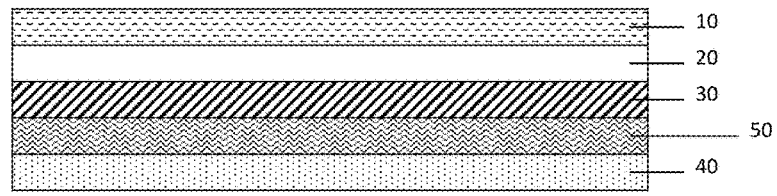
FIG. 1 is the schematic diagram of the hydrogel structure.
10 is the Polyurethane film layer
20 is the pressure sensitive adhesive layer
30 is the meltblown nonwoven
40 is the hydrogel
50 is the interpenetrating polymer network

The present invention relates to a hydrogel structure comprising: (a) a one way penetrating polyurethane film layer; (b) a hydrophobic pressure sensitive adhesive layer; (c) a multi-directional elastic meltblown nonwoven; (d) an interpenetrating polymer network; and (e) a hydrogel; wherein the meltblown nonwoven and the hydrogel are laminated by UV curing to form the interpenetrating polymer network, part of fibers of the meltblown nonwoven are exposed and fit stably with the pressure sensitive adhesive film.

DETAIL DESCRIPTION OF THE INVENTION

The present invention provides a hydrogel structure for multiple traumas. The structure has better swollen properties; the surface stickiness changes based on the status of moisture aborting and can create the best healing environment. The hydrogel structure makes the wound dressing to keep a suitable environment for wound healing, shorten the healing time, antiseptic and reduce the chances of being infected.

Hence, The present invention provides a hydrogel structure comprising: (a) a one way penetrating polyurethane film layer; (b) a hydrophobic pressure sensitive adhesive layer; (c) a multi-directional elastic meltblown nonwoven; (d) an interpenetrating polymer network; and (e) a hydrogel; wherein the meltblown nonwoven and the hydrogel are laminated by UV curing to form the interpenetrating polymer network, part of fibers of the meltblown nonwoven are exposed and fit stably with the pressure sensitive adhesive film.

In one embodiment, the interpenetrating polymer network strengthens tension and adhesive ability for wound covering.

In another embodiment, the hydrogel absorb excess moisture or wound tissue fluid to maintain proper skin moisture.

In still another embodiment, the hydrogel have an elongation rate from 200% to 1000%.

In still another embodiment, the hydrogel have an elongation rate from 881% to 960%.

In still another embodiment, the hydrogel comprises: (a) a monomer; (b) a plasticizer; (c) a photoinitiator; (d) a cross-linking agent; and (e) a thickener.

In still another embodiment, the monomer is acrylic amide monomer or acrylic sulfonate monomer.

In still another embodiment, the acrylic sulfonate monomer provides the hydrogel antiseptic effect.

In still another embodiment, the plasticizer is glycerol.

In still another embodiment, the thickener is glycerol.

In still another embodiment, the glycerol provides the hydrogel flexibility and increases the hydrophilicity.

In still another embodiment, the photoinitiator generates free radical and completes polymerization under 1 to 50 seconds of UV light irradiating.

In still another embodiment, the cross-linking agents are esters with unsaturated double functional groups.

In still another embodiment, the weight ratios of the hydrogel are: 15 to 30 units of acrylic amide monomer; 10 to 50 units of acrylic sulfonate monomer; 15 to 45 units of glycerol; 0.01 to 0.1 units of photoinitiator; and 0.01 to 0.2 units of unsaturated double functional groups ester monomer.

The meltblown nonwoven and the hydrogel of the present invention are irradiated by UV light, making them stuck together and formed an interpenetrating polymer network. The meltblown nonwoven fibers of the interpenetrating polymer network are hydrophobic and parts of them are exposed that can fit stably with the pressure sensitive adhesive layer and give the hydrogel multi-directional elasticity to adapt different skin parts.

The interpenetrating polymer network includes part of the elastic meltblown non-woven, therefore strengthens tension. In this case, while the polyurethane film achieves multi-directional elasticity for proper wound covering, the hydrogel remain unbroken because of the better tension.

The interpenetrating polymer network also strengthens adhesive ability. The hydrogel itself is easy to detach when absorbing liquid. However, since the interpenetrating polymer network includes part of the meltblown non-woven, better adhesion to skin is provided. As such, it avoids easy detachment which causes secondary damage.

The UV curing step could also be achieved by other oxygen related procedure.

The hydrogel of the present invention contacts with the trauma as the fitting surface of the wound, making the wound in the appropriate moist condition for accelerating healing. The moist healing environment is conducive to wound healing, if the wound dehydrates, the cells cannot survive. Although a variety of moist gauze or bandage can also provide a moist healing environment, the gauze or bandage type of dressings are required frequently change, making newly formed cells damaged easily, causing the wound second damage, and there is the risk of dehydration. The hydrogel of the present invention has the water-absorbing and sticky reducing features, and causes less damage compared to normal moist gauze or bandage such as Vaseline gauze in changing the dressings. Its water absorption ratio gives it the best moist condition that meets the requirements for wound healing. It absorbs excess moisture, keeping skin in proper humidity, and has more loading capacity for medicine.

The polyurethane film layer of the present invention is a tension, waterproof, breathable one way penetrating membrane; it provides thermoplastic deformable elasticity and tensioning that meets various needs of the wound cover. Meanwhile, the polyurethane film layer provides waterproof, bacteria resistance, breathable and cooling effects for the wound. The pressure sensitive adhesive layer of the present invention is a hydrophobic material coated on the polyurethane film layer, making it fit with the skin.

The present invention can be applied on all kinds of wound dressings, dressings for ring circumcision surgery, and electrode dressings.

The beneficial effects of the present invention are that the hydrogel structure can make trauma dressings multi-directional elastic to meet the use for many wounds, providing a better environment for wound healing, shorten the healing time, antiseptic and reduce the chances of being infected.

The following combined figures and specific implementing modalities that give the present invention further elaborations.

EXAMPLES

The examples below are non-limiting and are merely representative of various aspects and features of the present invention.

Example 1

The Hydrogel Structure

As shown in FIG. 1, the hydrogel structure had superimposed layers of the polyurethane film layer (10), the pressure sensitive adhesive layer (20), the meltblown nonwoven (30) and the hydrogel (40) that formed a interpenetrating polymer network (50), wherein the pressure sensitive adhesive layer (20) was coated on the polyurethane film layer (10), the meltblown nonwoven (30) and the hydrogel (40) were laminated by UV curing to make an interpenetrating polymer network (50), and part of the meltblown nonwoven fibers (30) were exposed and fit stably with the pressure sensitive adhesive layer (20) to form the hydrogel structure.

Example 2

The Hydrogel Formulation

The hydrogel was made by the steps as follows:

(a) providing a mixture comprising: (I) mixing the photoinitiator and the acrylic amide monomer to dissolve; (II) adding glycerol and mix to dissolve; (III) adding acrylic sulfonate monomer and mix to dissolve; (IV) adding glycerol and mix up.

(b) further providing a mixture comprising: (I) mixing the photoinitiator and the unsaturated double functional groups ester monomer.

(c) mixing up the mixture of step (a) and step (b).

(d) crosslinked polymerizing the mixture of step (c) by UV light irradiating to form the hydrogel.

The weight ratios of the above were

| | |
|---|---|
| Acrylic amide monomer | 15 to 30 units |
| Acrylic sulfonate monomer | 10 to 50 units |
| Glycerol | 15 to 45 units |
| Photoinitiator | 0.01 to 0.1 units |
| Unsaturated double functional groups ester monomer | 0.01 to 0.2 units |

Example 3

Tensile Test

For the hydrogel structure (LexiDerm) of the present invention, the polyurethane film layer and the hydrogel composites were examined based on ASTM D 412-98a Standard Test Methods for Vulcanized Rubber and Thermoplastic Elastomers-Tension, the results were as Table 1:

TABLE 1

Tensile strength and elongation test (Examining Unit: TTRI)

| Sample/Number | Maximum strength Max (g) | Fracture strength (g) | 100% Modules (g/mm²) | 300% Modules (g/mm²) | Tensile strength (g/mm²) | Elongation % |
|---|---|---|---|---|---|---|
| Polyurethane film layer/1 | 505.00 | 501.00 | 21.55 | 12.00 | 126.25 | 912.60 |
| Polyurethane film layer/2 | 1004.00 | 1004.00 | 25.56 | 13.43 | 251.00 | 1016.70 |
| Polyurethane film layer/3 | 1130.00 | 1130.00 | 24.34 | 11.98 | 282.50 | 1213.30 |
| Polyurethane film layer/4 | 661.00 | 647.00 | 26.26 | 12.85 | 165.25 | 950.05 |
| Polyurethane film layer/5 | 974.00 | 974.00 | 25.06 | 12.57 | 243.50 | 1111.70 |
| Polyurethane film layer/6 | 830.00 | 830.00 | 19.63 | 11.48 | 207.50 | 1113.10 |
| Hydrogel composites/1 | 354.00 | 321.00 | 43.27 | 19.69 | 141.60 | 925.63 |
| Hydrogel composites/2 | 304.00 | 256.00 | 33.15 | 17.68 | 121.60 | 886.30 |
| Hydrogel composites/3 | 289.00 | 263.00 | 26.56 | 13.75 | 115.60 | 935.05 |
| Hydrogel composites/4 | 304.00 | 258.00 | 29.08 | 16.03 | 121.60 | 881.20 |
| Hydrogel composites/5 | 287.00 | 221.00 | 29.59 | 17.43 | 114.80 | 907.02 |
| Hydrogel composites/6 | 413.00 | 306.00 | 37.56 | 21.75 | 165.20 | 959.95 |

Example 4

Breathability Test

For the hydrogel structure (LexiDerm) of the present invention, the polyurethane film layer and the hydrogel composites were examined based on JIS L 1096, the results were as Table 2:

TABLE 2

Breathability test (Examining Unit:TTRI)

| Number | Polyurethane film layer (cm³/cm²/sec) | Hydrogel composites (cm³/cm²/sec) |
|---|---|---|
| 1 | 0.0035 | 0.0520 |
| 2 | 0.0028 | 0.0759 |
| 3 | 0.0035 | 0.0590 |
| 4 | 0.0030 | 0.0695 |
| 5 | 0.0028 | 0.0605 |
| 6 | 0.0025 | 0.0510 |

Example 5

Moisture Permeability Test

For the hydrogel structure (LexiDerm) of the present invention, the moisture permeability were examined based on JIS L 1099 A1 Calcium Chloride upright Cup test, the results were as Table 3:

Permeability (g/m² day)=(Second−First)*8488

TABLE 3

Permeability test (Examining Unit:TTRI)

| Sample/Number | First weight (g) | Second weight (g) | Result (g/m² day) |
|---|---|---|---|
| Hydrogel composites/1 | 230.138 | 230.893 | 6408.44 |
| Hydrogel composites/2 | 230.914 | 231.58 | 5653.008 |
| Hydrogel composites/3 | 230.718 | 231.388 | 5686.96 |
| Hydrogel composites/4 | 238.172 | 239.04 | 7367.584 |
| Hydrogel composites/5 | 230.423 | 231.124 | 5950.088 |
| Polyurethane film layer/1 | 227.869 | 227.963 | 797.872 |
| Polyurethane film layer/2 | 234.092 | 234.198 | 899.728 |
| Polyurethane film layer/3 | 226.27 | 226.373 | 874.264 |
| Polyurethane film layer/4 | 224.309 | 224.417 | 916.704 |
| Polyurethane film layer/5 | 228.073 | 228.179 | 899.728 |

Example 6

Absorption Rate

Figure 2:
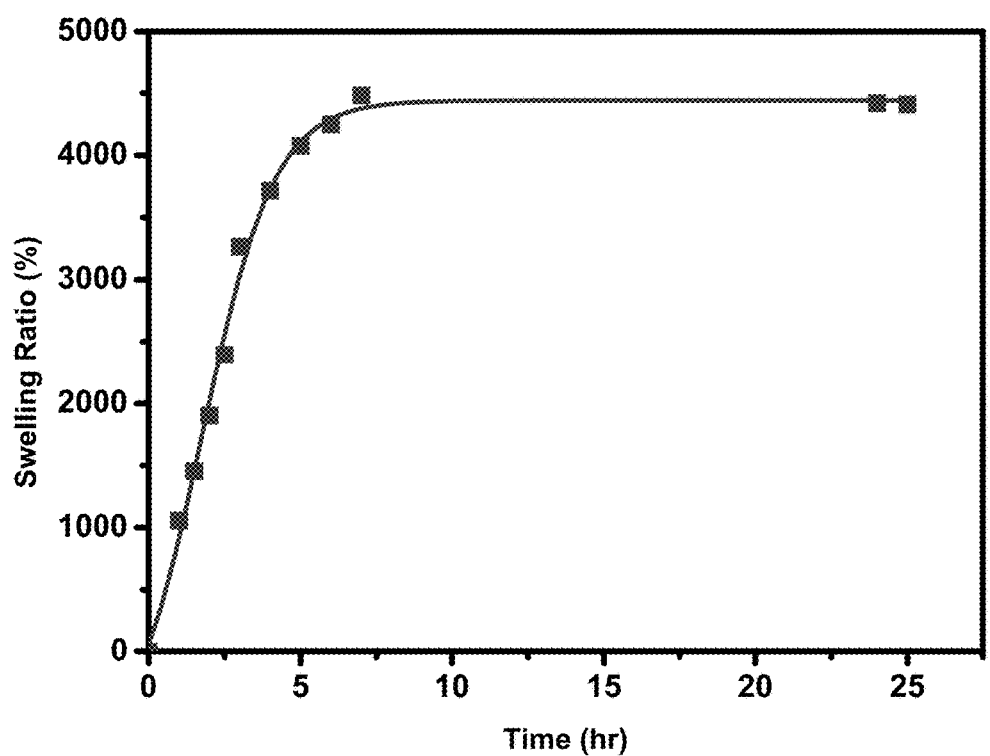
FIG. 2 is the swelling ratio of the hydrogel (%).

For the hydrogel structure (LexiDerm) of the present invention, the absorption rate were examined. The hydrogel were weighted and put it into 25° C., pH=7.4 PBS, after fully swelled, the surface water was wiped out and the hydrogel were weighted. The hydrogel were removed every time interval and were weighted till the weight of the hydrogel stopped changing. The absorption rate was measured by the change of the hydrogel weight, the swelling rate %=[(weight of the wet hydrogel−weight of the original hydrogel)/weight of the original hydrogel]×100%, the results are as FIG. 2.

Example 7

Wound Healing Test

Materials and Methods
(1) Test Objects
Gauze Control Group
The hydrogel structure of present invention experimental group (LexiDerm)
(2) Experimental Animals
Three animal strains of LYD 2 months old pigs that have passed the examination of experimental animal and Management Group of Taichung veterans general hospital (Number: La99736).
(3) Test Group
Animals were divided into two groups, Day 14 (three pigs) and Day 31 (one pig). Every animal had three 3 cm×3 cm all skin excision wounds on left and right side of the back respectively, then giving the control or experimental dressings respectively.
(4) Applying Methods
Applied the experimental or control substances directly on the wound on animals' back, and changed the substances every 3-5 days.
(5) In Vivo Animal Experiments Experiments carried out on 2 months old LYD three strains of pigs as experimental animals. Experimental equipments included shaving knife, autoclaved with high temperature and pressure surgical instruments (ratio scale, hole towel forceps, scissors, tweezers, clamps, scalpel and needle holder) and consumables (sterile hole towel, gauze, cotton, tincture of iodine, alcohol and sutures), the procedures were as follows:

Each pig was giving leading anesthesia by ketamine (20 mg/kg) and xylazine (2 mg/kg), then by 1.0-2.0% isoflurane to maintain anesthesia. After shaving the back, sterilize with 70% Alcohol first, then with Betadine and covered with sterilized hole towels. Six 3 cm×3 cm all skin excision wounds with the depth to panniculus carnosis were created by scalpel. Covered the wounds with experimental or control dressings then with a layer of gauze and wrapped the wounds with elastic bandages or sutures to prevent infection caused by the broken of the dressings. Cleaned the wounds every 3-5 days after the surgery, changed new experimental or control dressings and then re-bandaged and fixed by the above methods. Postoperative care: In first 1-2 days, conducted postoperative analgesia by carprofen 2 mg/kg to relieve pain.

Figure 3:
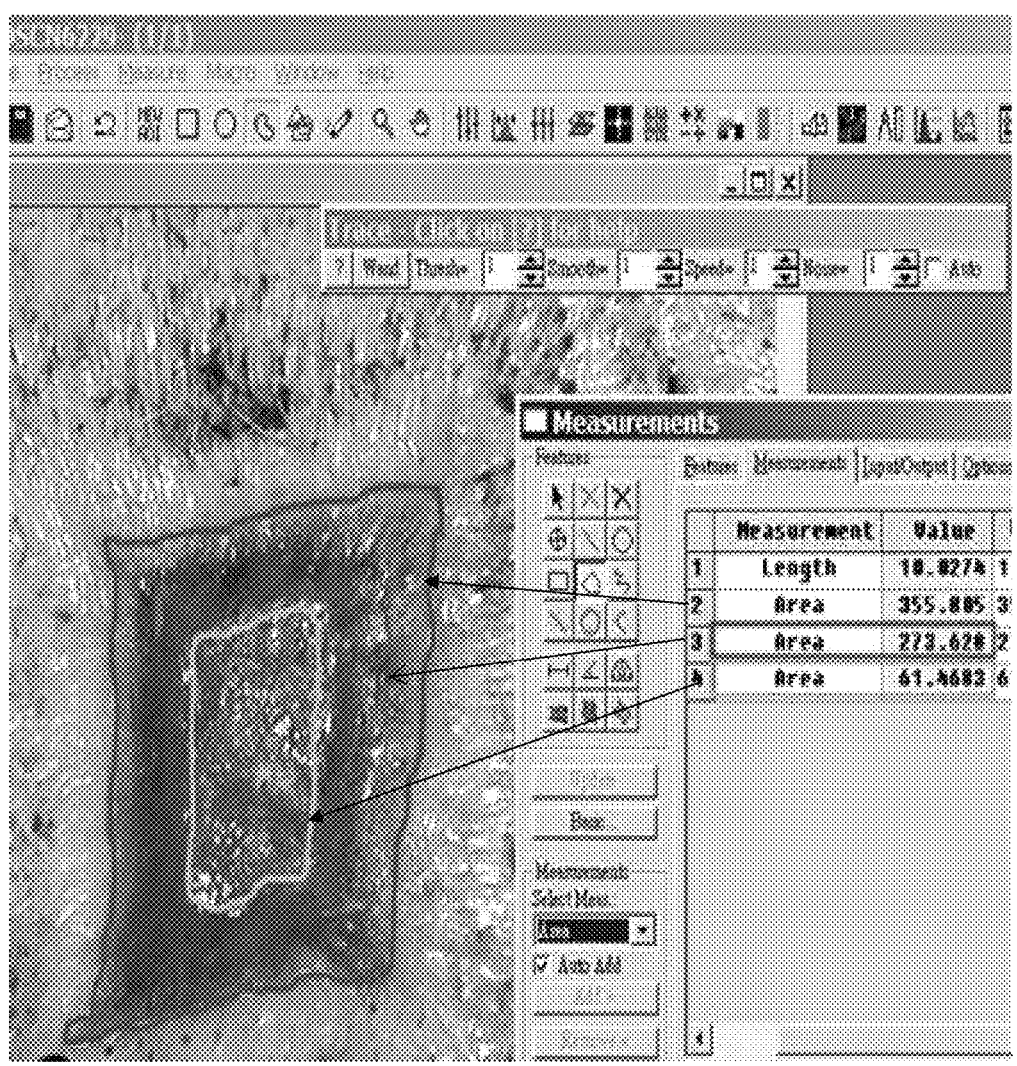
FIG. 3 is the wound area calculated by the software Image Pro Plus 4.5 (Area 2, value 355.096).

As mentioned above, the pigs should be fed separately, free to water and feed regularly after the operation. The experiments were recorded by day and evaluated the pigs as follows on Day 3, 7, 10, 12 after the operation. Clinical wound assessment—observed the skin and wound healing process. Record the dressing binding situation on the pigs separately, the amount of secretion, the situation of the wound surrounding tissue, the growth situation of the wound and the changing difficulty of the dressings. In addition to text recording, took pictures for comparison and finally arranged and analyzed the results. Wound healing promoting assessment—put a ratio scale and took pictures of the wounds on each dressing changing point. Calculated the wound area after the correction of graphics software Image Pro Plus 4.5 by the ratio scale, as shown in FIG. 3, in which Area 2 was the entire wound area, the calculated value was 355.095; Area 4 was part of the wound area still in healing, the calculated value was 61.4683, and Area 3 was the partially healed wound area, the calculated value was 355.096 (Area 2)−61.4683 (Area 4)=273.628).

Histological assessment—took out the normal tissue together with the implanted samples and underwent histopathological biopsy (if required). 14 days after the surgery, took 5 mm wedge biopsies, need to include the dressing, granulation tissue, connective tissue and the muscle below. Fix tissues in formaldehyde first, then underwent dehydrate, embedding, de-wax, slice and stained with H & E and picro-Sirius red. Observe the interaction of epithelial cells, dermal cells, neovascularblasts, inflammatory cells and fibroblasts to assess wound healing.

Scoring Standard:

Epidermis growing score: 0—No growth, 1—The growth of epidermis is smaller than $1/3$ of the wound, 2—The growth of epidermis is between $1/3$ and $1/2$ of the wound, 3—The growth of epidermis is between $1/2$ and $2/3$ of the wound, 4—The growth of epidermis is more than $2/3$ of the wound or completely healed.

Granulation score: 0—No growth of granulation tissue, 1—Loose growth of granulation tissue, 2—Dense growth of granulation tissue, 3—Connective tissue formed. Inflammation score: 0—Severe inflammatory response (large infiltration of neutrophils and lymphocytes), 1—Moderate inflammatory response (multi infiltration of lymphocytes), 2—Mild inflammatory response (small infiltration of lymphocytes), 3—No inflammatory response (no infiltration of lymphocytes).

Results:

(1) Postoperative Clinical Symptoms and Wound Observation Assessment

The first 1 to 2 days after pigs were conducted whole skin excision, giving them Capricorn 2 mg/kg for postoperative pain relieving by the principles of human experiments. During the experiment, pigs didn't show biting the wound portion and no dressing falling or frayed. On the dressing changing day, 3 and 6 days after the surgery, the dressings could not fully absorb the wound exudates and there were large amounts of exudates flowing out around the wounds in experimental and gauze control groups. The amounts of exudates were significantly reduced on the dressing changing day, 9 days after the surgery. In the adhesion condition between dressings and wounds, the gauzes adhered to the wound tissues easily and needed to rinse with saline solution to take them out during the experiment in the control group, but the dressings of the experimental group didn't have this situation.

(2) Postoperative Wound Healing Visual Assessment

Figure 4:
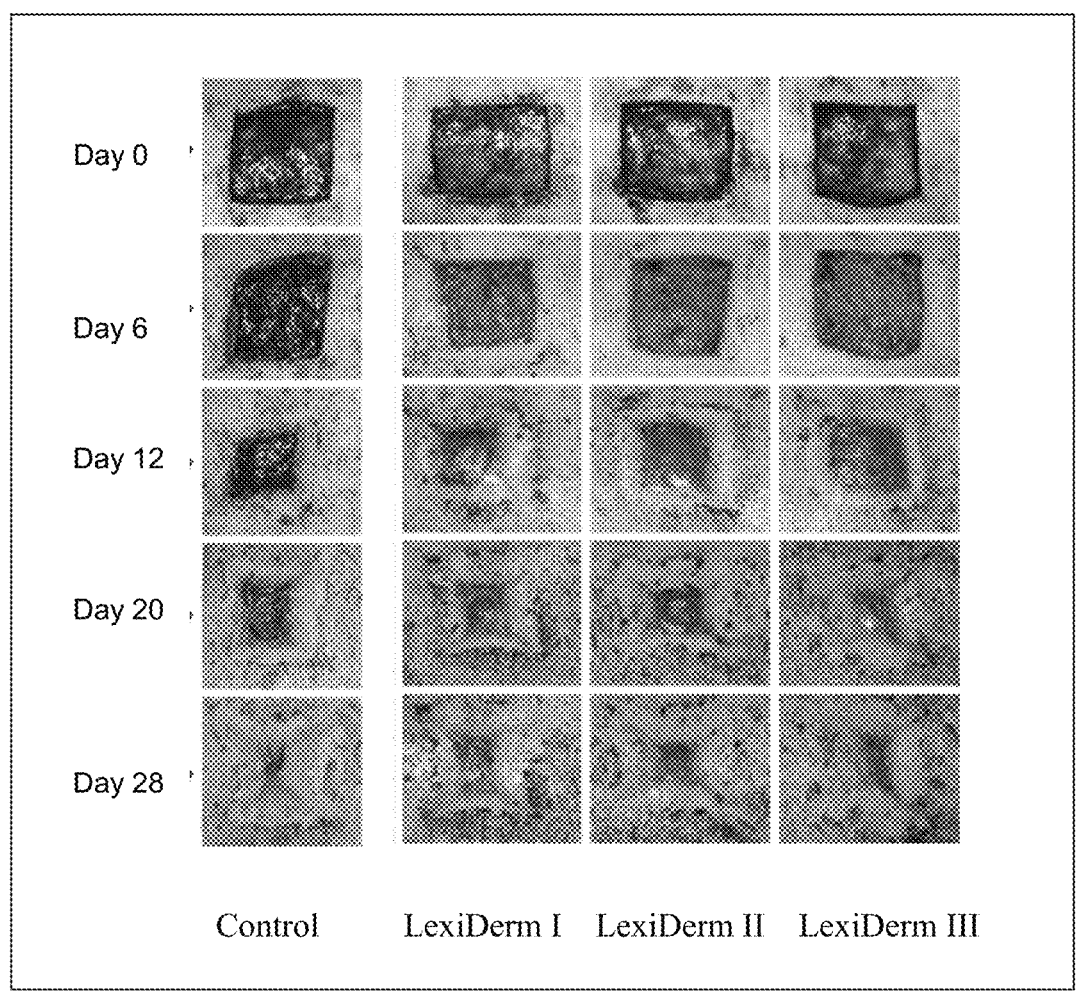
FIG. 4 is the appearance of the wound on different timing after the dressings are applied.

The sizes of the wounds after conducted whole skin excision in pigs were between 28.72 to 32.52 $mm^2$ 6 days after dressings were applied; there was a little new skin tissue formed on the edge of the wound in the experimental group (FIG. 4, day 6). 12 days later, the wounds in each group were significantly reduced and the wound shapes were square and smooth. The newly formed skin tissue covered more than $1/2$ of the wound in the experimental group on day 20. 28 days after dressings were applied; almost all the wounds had healed. The healing of the wounds in the gauze control group was mainly the distortion of the wound and few skin tissues were formed. However, in the experimental group, there were more new skin tissues formed, but the newly formed skin tissues of the wound were smooth (FIG. 4, day 28).

(3) Postoperative Wound Promoting Healing Assessment

Figure 5:
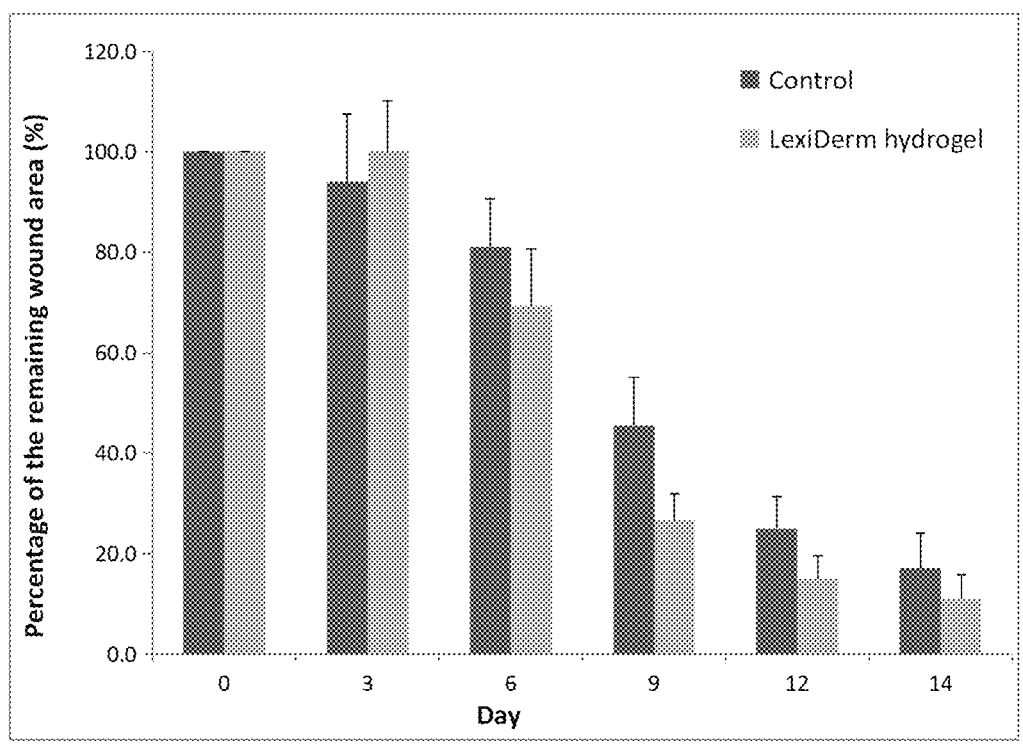
FIG. 5 is the percentage of the remaining wound area (%) after applying the dressings 14 days.

After quantitative analysis of wound area, we could see the wounds were significantly reduced in the experimental group compared to gauze control group on day 6 of dressing applied (FIG. 5 and Table 4).

TABLE 4

| Group | 0 day | 3 day | 6 day | 9 day | 12 day | 14 day |
|---|---|---|---|---|---|---|
| Control | 100 ± 0.0 | 94.0 ± 13.5 | 81.0 ± 9.6 | 45.4 ± 9.7 | 25.0 ± 6.3 | 17.2 ± 6.9 |
| LexiDerm hydrogel | 100.0 ± 0.0 | 100.1 ± 9.9 | 69.4 ± 11.2 | 26.6 ± 5.3 | 15.0 ± 4.6 | 11.0 ± 4.8 |

The percentage of the remaining wound area to the original area after applying the dressings 14 days (%).
*: $P < 0.05$, : $P < 0.01$, *: $P < 0.001$ Compared to the control group. Control (n = 3), LexiDerm hydrogel (n = 9).

(4) Histological Assessment of the Wound 14 Days after Applying Dressings

Figure 6:
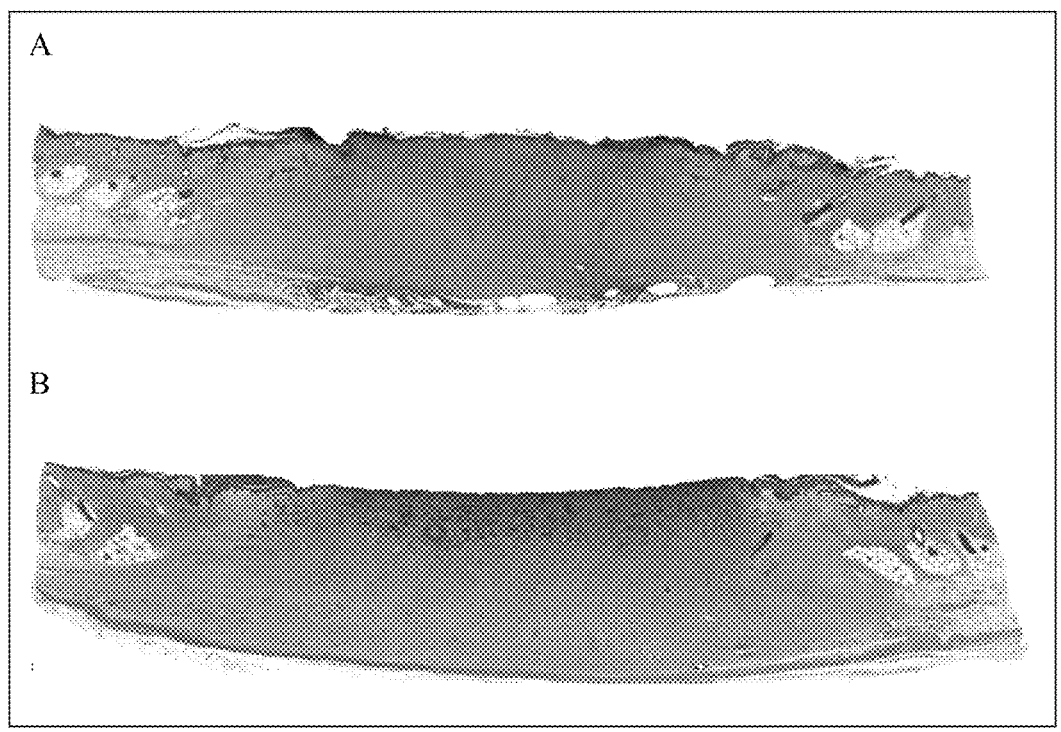
FIG. 6 is the representative figures of epidermal growth after applying the dressings 14 days. A represents the control group. B represents LexiDerm Hydrogel Dressing.
Figure 7:
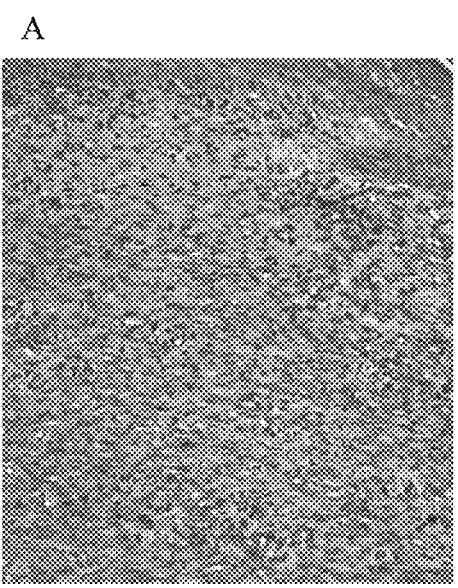
FIG. 7 is the representative figures of granulation growth and Inflammation after applying the dressings 14 days. A represents the control group. B represents LexiDerm Hydrogel Dressing.
Figure 7:
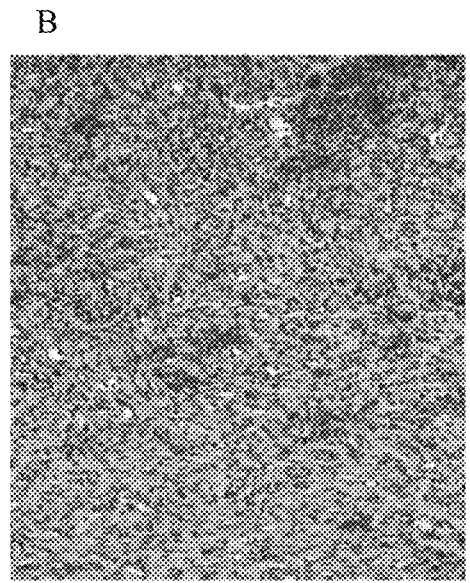
Figure 8:
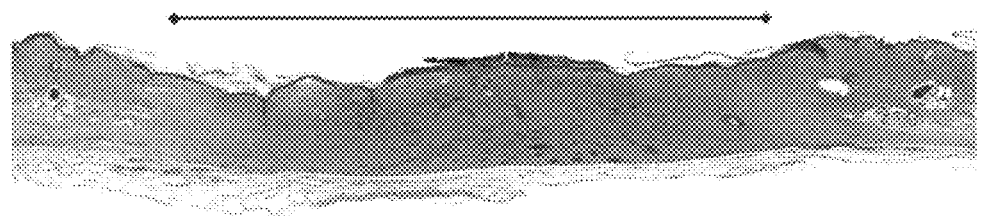
FIG. 8 is the representative figures of epidermal growth after applying the dressings 31 days. A represents the control group. B represents LexiDerm Hydrogel Dressing.
Figure 8:
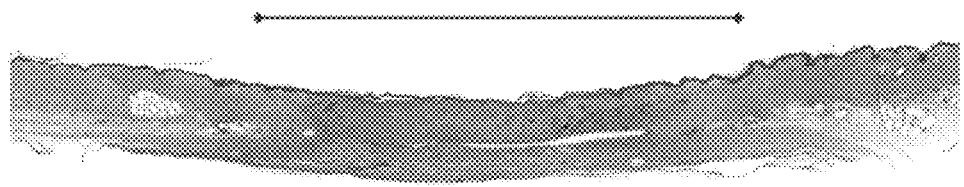
Figure 9:
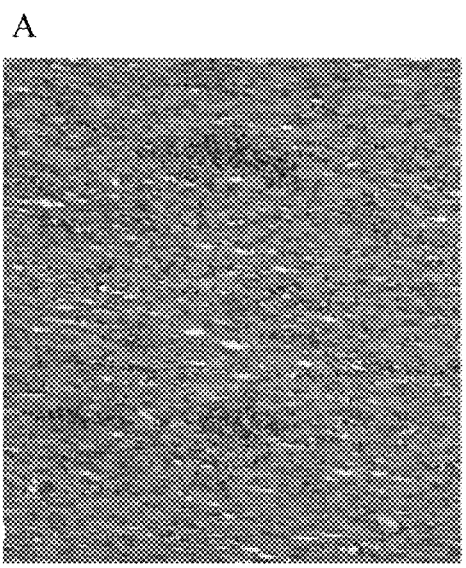
FIG. 9 is the representative figures of granulation growth and Inflammation after applying the dressings 31 days. A represents the control group. B represents LexiDerm Hydrogel Dressing.
Figure 9:
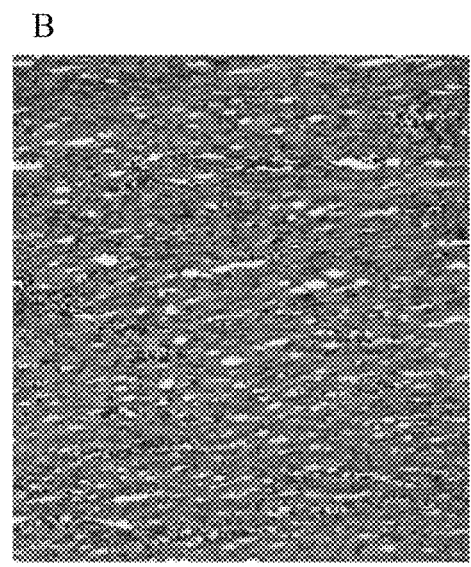

Epidermis growing score: In the gauze control group, the growth of epidermis was near ⅓ of the wound and the score was 1. In other experimental groups, the growth of epidermis was between ⅓ and ½ of the wound, and the score was 2. The growth of epidermis in the experimental group was better than in the gauze control group (FIG. 6). Granulation score: The growth of granulation tissue in gauze control and experimental group was very dense and both the scores were 2 (FIG. 7). Inflammation score: The infiltration of lymphocytes in the gauze control group wasn't significant, and the wounds of the experimental group had small to medium lymphocyte infiltration. The endogenous in the experimental group was significant to the gauze control group (FIG. 7).

Example 8

Bacterial Preventing and Antiseptic Test

For the hydrogel structure (LexiDerm) of the present invention, the bacterial preventing and antiseptic effects were examined based on JIS L1902:2008, the results were as Table 5 (strain: *Staphylococcus*) and Table 6 (strain: *Klebsiella pneumoniae*):

TABLE 5

| Test Article | | Result | |
|---|---|---|---|
| | | Control | LexiDerm |
| *Staphylococcus* ATCC 6538P | Bacterial planting concentration | $1.8 \times 10^5$ | $1.8 \times 10^5$ |
| | Ma [1] | $3.9 \times 10^4$ | — |
| | Mb [2] | $1.4 \times 10^7$ | — |
| | Mo [3] | — | $2.8 \times 10^4$ |
| | Mc [4] | — | <20 |
| | Proliferation value [5] | 2.6 | — |
| | Antiseptic activity value [6] | — | 5.7 |
| | Bactericidal activity value [7] | — | 3.3 |

* The test base on JIS L1902:2008
[1] Ma = The amount of bacteria immediately after washing in the control group
[2] MB = The amount of bacteria 18 hours after culture in the control group
[3] Mo = The amount of bacteria immediately after washing in the experimental group
[4] Mc = The amount of bacteria 18 hours after culture in experimental group
[5] Proliferation value = logMb − logMa
[6] Antiseptic activity value = (logMb − logMa) − (logMc − logMo)
[7] Bactericidal activity value = logMa − logMc
Source: TTRI Report 2010/07

TABLE 6

| Test Article | | Result | |
|---|---|---|---|
| | | Control | LexiDerm |
| *Klebsiella pneumoniae* ATCC 6538P | Bacterial planting concentration | $1.6 \times 10^5$ | $1.6 \times 10^5$ |
| | Ma [1] | $2.8 \times 10^4$ | — |
| | Mb [2] | $2.0 \times 10^7$ | — |
| | Mo [3] | — | $2.9 \times 10^4$ |
| | Mc [4] | — | <20 |
| | Proliferation value [5] | 2.9 | — |
| | Antiseptic activity value [6] | — | 6.0 |
| | Bactericidal activity value [7] | — | 3.2 |

* The test base on JIS L1902:2008
[1] Ma = The amount of bacteria immediately after washing in the control group
[2] MB = The amount of bacteria 18 hours after culture in the control group
[3] Mo = The amount of bacteria immediately after washing in the experimental group
[4] Mc = The amount of bacteria 18 hours after culture in experimental group
[5] Proliferation value = logMb − logMa
[6] Antiseptic activity value = (logMb − logMa) − (logMc − logMo)
[7] Bactericidal activity value = logMa − logMc
Source: TTRI Report 2010/07

What is claimed is:

1. A hydrogel structure comprising:
    (a) a one way penetrating polyurethane film layer;
    (b) a hydrophobic pressure sensitive adhesive layer;
    (c) a multi-directional elastic meltblown nonwoven layer;
    (d) an interpenetrating polymer network; and
    (e) a hydrogel layer;
    wherein four layers, (a), (b), (c) and (e), are arranged in a sequential order, and the interpenetrating polymer network is formed by interpenetrating part of the meltblown nonwoven layer into the hydrogel layer and part of the hydrogel layer into the meltblown nonwoven layer by UV curing, thereby the remaining meltblown nonwoven layer being laminated with the pressure sensitive adhesive layer such that the (b), (c) and (e) layers being bound together by the interpenetrating polymer network.

2. The hydrogel structure of claim 1, wherein the hydrogel comprising:
    (a) a monomer;
    (b) a plasticizer;
    (c) a photoinitiator;
    (d) a cross-linking agent; and
    (e) a thickener.

3. The hydrogel structure of claim 2, wherein the thickener is glycerol.

4. The hydrogel structure of claim 2, wherein the photoinitiator generates free radical and completes polymerization under 1 to 50 seconds of UV light irradiating.

5. The hydrogel structure of claim 2, wherein the cross-linking agents are esters with unsaturated double functional groups.

6. The hydrogel structure of claim 2, wherein the ratio by weight of the acrylic amide monomer, the acrylic sulfonate monomer, the glycerol, the photoinitiator, and a monomer of the esters with unsaturated double functional groups is from 15:10:15:0.01:0.01 to 30:50:45:0.1:0.2.

7. The hydrogel structure of claim 2, wherein the monomer is acrylic amide monomer or acrylic sulfonate monomer.

8. The hydrogel structure of claim 7, wherein the acrylic sulfonate monomer provides the hydrogel antiseptic effect.

9. The hydrogel structure of claim 2, wherein the plasticizer is glycerol.

10. The hydrogel structure of claim 9, wherein the glycerol provides the hydrogel flexibility and increases the hydrophilicity.

11. The hydrogel structure of claim 1, wherein the hydrogel have an elongation rate from 200% to 1000%.

12. The hydrogel structure of claim 11, wherein the hydrogel have an elongation rate from 881% to 960%.

13. The hydrogel structure of claim 1, wherein the interpenetrating polymer network strengthens tension and adhesive ability for wound covering.

14. The hydrogel structure of claim 1, wherein the hydrogel absorb excess moisture or wound tissue fluid to maintain proper skin moisture.

* * * * *